United States Patent
Kitamura et al.

[11] Patent Number: 6,153,793
[45] Date of Patent: Nov. 28, 2000

[54] METHOD FOR PRODUCING AN N-ALKYL-ALPHA-DIALKYL-AMINOACETHOHYDROXAMIC ACID COMPOUND

[75] Inventors: Masaharu Kitamura; Daisuke Urazoe; Hideto Mori; Akio Satoh, all of Odawara, Japan

[73] Assignee: Fuji Photo Film, Ltd., Minami-ashigari, Japan

[21] Appl. No.: 09/352,679

[22] Filed: Jul. 14, 1999

[30] Foreign Application Priority Data

Jul. 14, 1998 [JP] Japan ................................. 10-198911

[51] Int. Cl.$^7$ .................................................. C07C 259/04
[52] U.S. Cl. ............................................................ 562/623
[58] Field of Search ............................................. 562/623

[56] References Cited

U.S. PATENT DOCUMENTS 5,015,763 5/1991 Ono ........................................ 562/106

FOREIGN PATENT DOCUMENTS

B699382 12/1994 Japan .
63-316743 12/1998 Japan .

OTHER PUBLICATIONS

M. Ono, Journal of Synthetic Organic Chemistry, Japan, vol. 47, pp. 795–812 (1989).
M. Ono et al., Tetrahedron Lett., vol. 30, No. 2, pp. 207–210 (1989).

*Primary Examiner*—Samuel Barts
*Assistant Examiner*—Brian J. Davis
*Attorney, Agent, or Firm*—Birch, Stewart, Kolasch & Birch, LLP

[57] ABSTRACT

There is disclosed a method for producing an N-alkyl-α-dialkylaminoacetohydroxamic acid compound represented by formula (2), which comprises reacting an α-dialkylaminoacetic acid ester compound represented by formula (1) with an N-alkylhydroxylamine, wherein the reaction is carried out in water and an ether-series organic solvent,

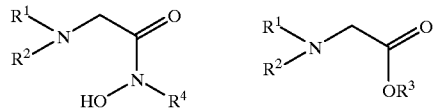

wherein $R^1$, $R^2$, $R^3$ and $R^4$, which are the same or different, each represents an alkyl group. According to the method, it is possible to obtain the objective compound in a high yield with a short reaction time, with restrained formation of a by-product.

14 Claims, No Drawings

METHOD FOR PRODUCING AN N-ALKYL-ALPHA-DIALKYL-AMINOACETHOHYDROXAMIC ACID COMPOUND

FIELD OF THE INVENTION

The present invention relates to a method for producing an N-alkyl-α-dialkylaminoacetohydroxamic acid compound that is useful as, for example, a deacylation agent.

BACKGROUND OF THE INVENTION

N-alkyl-α-dialkylaminoacetohydroxamic acid derivatives are highly selective reagents that are useful for the deacylation of esters in an organic solvent under a substantially neutral condition [Journal of Synthetic Organic Chemistry, Japan (Yuki Goseikagaku Kyokai Shi), Vol. 47, 795 (1989); Tetrahedron Lett., 30, 207 (1989); JP-A-63-316755 (the term "JP-A" as used herein means an unexamined published Japanese patent application); JP-B-6-99382 (the term "JP-B" as used herein means an examined Japanese patent publication), JP-A-63-316743]. In JP-B-6-99382, as a typical example, a method for producing an N-methyl-α-dimethylaminoacetohydroxamic acid is described, and the specification thereof discloses a method for reacting N,N-dimethylglycine methyl ester with N-methylhydroxylamine hydrochloride, in the presence of sodium hydroxide, in a mixed solvent consisting of water and methanol.

It is difficult to say that such a conventional method is satisfactory, because the reaction time at room temperature according to the conventional method is as long as 7 days, which results in increased production cost. Further, our investigation made clear that hydrolysis of N,N-dimethylglycine methyl ester, as a raw material, occurs as a side reaction under the above-described reaction conditions, and consequently it causes a problem. That is, the conventional method necessitates a particular operation in order to remove N,N-dimethyl glycine as a by-product, and the same is not advantageous to a practical method in consideration of a processing amount, the number of persons required, the time required, and reduction in a yield of the objective compound. As a result, the development of an efficient and advantageous production method that causes no side-reaction has been desired.

SUMMARY OF THE INVENTION

Accordingly, an object of the present invention is to provide a method for producing an N-alkyl-α-dialkylaminoacetohydroxamic acid compound, in which the reaction time is short, formation of a by-product is restrained, and an objective compound is obtained in a high yield.

Other and further objects, features, and advantages of the invention will appear more fully from the following description.

DETAILED DESCRIPTION OF THE INVENTION

As a result of our intensive investigation about an industrial method for producing an N-alkyl-α-dialkylaminoacetohydroxamic acid compound in view of the above-described situation, we have found that the desired N-alkyl-α-dialkylaminoacetohydroxamic acid compound can be obtained effectively and unexpectedly, by carrying out a reaction in a mixture system comprising water and a particular ether-series organic solvent, whereby the present invention has been accomplished.

That is, according to the present invention, there are provided:

(1) A method for producing an N-alkyl-α-dialkylaminoacetohydroxamic acid compound represented by formula (2):

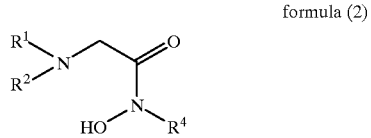

formula (2)

wherein $R^1$ and $R^2$, which are the same or different, each represent an alkyl group, and $R^4$ represents an alkyl group, which comprises reacting an α-dialkylaminoacetic acid ester compound represented by formula (1):

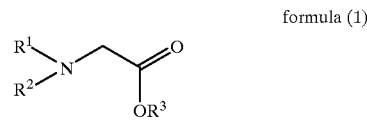

formula (1)

wherein $R^1$ and $R^2$ each have the same meanings as those defined above, and $R^3$ represents an alkyl group, with an N-alkylhydroxylamine, wherein the reaction is carried out in a mixture system comprising water and an ether-series organic solvent;

(2) The method as stated in the above (1), wherein the ether-series organic solvent is at least one solvent selected from the group consisting of diethyl ether, diisopropyl ether, methyl t-butyl ether, diphenyl ether, 1,2-dimethoxyethane, 1,2-diethoxyethane, methoxybenzene, ethoxybenzene, tetrahydrofuran, and 1,4-dioxane;

(3) The method as stated in any one of the above (1) or (2), wherein the ether-series organic solvent is at least one solvent selected from the group consisting of 1,2-dimethoxyethane, 1,2-diethoxyethane, methoxybenzene, tetrahydrofuran, and 1,4-dioxane;

(4) The method as stated in any one of the above (1) to (3), wherein the reaction temperature is in a range of 20 to 80° C.; and (5) The method as stated in any one of the above (1) to (4), wherein the compound represented by formula (2) is N-methyl-α-dimethylaminoacetohydroxamic acid or N-methyl-α-diethylaminoacetohydroxamic acid.

The compounds represented by the above-described formulae are explained in detail. In the formulae, $R^1$, $R^2$, and $R^3$ each represent an alkyl group preferably having 1 to 6 carbon atoms, e.g. a methyl group, an ethyl group, an n-propyl group, an isopropyl group, an n-butyl group, and a cyclohexyl group, more preferably $R^1$, $R^2$, and $R^3$ each are a methyl group or an ethyl group. Preferable examples of the combination of $R^1$ and $R^2$ include the cases where both of them each are a methyl group at the same time, or an ethyl group at the same time. $R^3$ may be a methyl group or an ethyl group, with preference given to a methyl group.

Further, $R^4$ represents an alkyl group preferably having 1 to 7 carbon atoms. Examples of $R^4$ include a methyl group, an ethyl group, an n-propyl group, an isopropyl group, an n-butyl group, a cyclohexyl group, and a benzyl group. Of these groups, a methyl group is more preferred.

Next, specific examples of the compounds represented by formula (1) are illustrated below, but the present invention should not be construed as being limited to those.

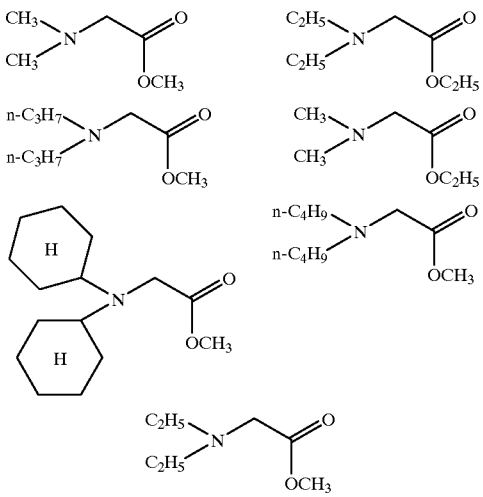

Next, the reaction conditions and the like that are applied in the production method of the present invention are described in detail. The method of the present invention is characterized in that a reaction is carried out in a mixture system of solvents that comprises water and an ether-series organic solvent. In the present invention, the mixture system comprising water and the ether-series organic solvent may contain another solvent such as an alcohol (e.g. methanol and ethanol) in such amount that does not give bad effect on the reaction. The mixture solvent system for use in the present invention preferably does not contain alcohols to prevent the reaction velocity from lowering.

Examples of the ether-series organic solvent include diethyl ether, diisopropyl ether, methyl t-butyl ether, diphenyl ether, 1,2-dimethoxyethane, 1,2-diethoxyethane, methoxybenzene, ethoxybenzene, tetrahydrofuran, and 1,4-dioxane. Of these solvents, 1,2-dimethoxyethane, 1,2-diethoxyethane, methoxybenzene, tetrahydrofuran, and 1,4-dioxane are preferably used. An amount of the solvent to be used can be suitably determined within a range in which reactants can be dissolved. Even though the amount thereof is not limited in particular, a ratio by weight of the solvent to an α-dialkylaminoacetic acid ester compound is generally from 0.3 to 100 times, preferably from 0.5 to 20 times, and more preferably from 0.5 to 5 times. There is no particular restriction on the mixing ratio of the solvent to water to be used in carrying out the reaction according to the method of the present invention, so long as operational problems through the work, such as incapability of agitation due to precipitation of crystals, are not caused, and further a progress of the reaction is not prohibited. The mixing ratio by volume of the organic solvent/water is generally from ½ to 1/20, and preferably from ⅕ to 1/20. For example, when methoxybenzene is used as the organic solvent, the mixing ratio by volume of the organic solvent/water is generally from ⅓ to 1/20, and preferably from ⅕ to 1/20. On the other hand, when 1,2-dimethoxyethane, 1,2-diethoxyethane, tetrahydrofuran, or 1,4-dioxane is used as the organic solvent, the mixing ratio by volume of the organic solvent/water is generally from ½ to 1/20, and preferably from ⅕ to 1/20.

The reaction is carried out in a temperature within the range of from 20 to 80° C., preferably from 30 to 70° C., and more preferably from 30 to 50° C. An N-alkylhydroxylamine as a reagent may be a free form or a salt thereof. Specific examples of the compound include N-methylhydroxylamine, N-methylhydroxylamine sulfate, N-methylhydroxylamine hydrochloride, N-ethylhydroxylamine hydrochloride, and N-benzylhydroxylamine hydrochloride. Of these compounds, N-methylhydroxylamine hydrochloride is preferably used. When an N-alkylhydroxylamine sulfate or an N-alkylhydroxylamine hydrochloride is used, the reaction is practiced in the coexistence of 0.9 to 1.2 equivalent, and preferably 1 equivalent of alkali, specifically sodium hydroxide, for neutralization. The number of equivalent of the N-alkylhydroxylamine to an α-dialkylaminoacetic acid ester compound represented by formula (1) is generally from 0.9 to 6.0 equivalents, preferably from 0.9 to 3.0 equivalents, and more preferably from 0.9 to 1.5 equivalents. The reaction time differs depending on a charged amount (preparation scale) and a reaction temperature, but generally it is in a range of 6 to 15 hours.

By practicing the reaction in a mixture system comprising water and an ether-series organic solvent as described above, the reaction is accelerated, and further, an undesired hydrolysis reaction is drastically restrained. On the other hand, the reaction never progresses in a single use of the ether-series organic solvent. Further, a single use of water as a solvent is disadvantageous in that a considerable amount of N,N-dialkylglycine, e.g. N,N-dimethylglycine, that is a hydrolysis product, is generated as a by-product.

Examples of the N-alkyl-α-dialkylaminoacetohydroxamic acid compound represented by formula (2) that is produced according to the method of the present invention, include N-methyl-α-dimethylaminoacetohydroxamic acid, N-methyl-α-diethylaminoacetohydroxamic acid, N-ethyl-α-dimethylaminoacetohydroxamic acid, N-benzyl-α-dimethylaminoacetohydroxamic acid, N-benzyl-α-di-n-propylaminoacetohydroxamic acid, N-cyclohexyl-α-dimethylaminoacetohydroxamic acid, N-ethyl-α-di-n-butylaminoacetohydroxamic acid, and N-methyl-α-dicyclohexylaminoacetohydroxamic acid. Of these compounds, N-methyl-α-dimethylaminoacetohydroxamic acid and N-methyl-α-diethylaminoacetohydroxamic acid are preferably produced according to the method of the present invention.

According to the method of the present invention, an N-alkyl-α-dialkylaminoacetohydroxamic acid compound that is useful as a deacylation agent, can be effectively produced.

The present invention will be described in more detail with reference to the following examples and comparative examples, but the invention should not be construed as being limited thereto.

EXAMPLES

Example 1

To 180 ml of water, 137.5 g of sodium hydroxide and 281.2 g of N-methylhydroxylamine hydrochloride were dissolved to form a solution, to which 18 ml of tetrahydrofuran was added. Subsequently, 358 g of N,N-dimethylglycine methyl ester was added thereto. The resultant reaction mixture was stirred at 40° C. for 9 hours in total. The results of gas chromatography demonstrated a rate of residual raw materials: 8.8%, a rate of formation of N-methyl-α-dimethylaminoacetohydroxamic acid: 88.2%, and a rate of secondary production of N,N-dimethylglycine:

2.1%. After the reaction mixture was cooled to room temperature, insoluble substances were removed by filtration. The thus-obtained filtrate was concentrated. To the resultant residue, 750 ml of isopropyl alcohol was added, and it was fully stirred, followed by filtration to remove insoluble substances. The thus-obtained filtrate was concentrated, and then the resultant residue was recrystallized from isopropyl alcohol/hexane (1/1) to give 275 g of pure N-methyl-α-dimethylaminoacetohydroxamic acid (yield: 69.4%). The data of various physical properties were identical with those described in JP-B-6-99382.

The conditions of gas chromatography used for reaction analysis and purity assay of the products were as follows:

Column: 50% (Cyanopropylphenyl)methylpolysiloxane 0.53 mm×30 m

Carrier-gas: Helium

Speed of running fluid: 33.9 ml

Detection: FID

Column temperature: 100° C.→200° C. (increase in temperature 10° C./min.)

Example 2

According to the method described in Example 1, 47.5 g of N-methylhydroxylamine hydrochloride, 23 g of sodium hydroxide, and 60 g of N,N-dimethylglycine methyl ester were reacted in a mixture solvent consisting of 55 ml of water and 5.5 ml of methoxybenzene, at 45° C. for 10 hours. The results of gas chromatographic analysis demonstrated a rate of residual raw materials: 10.1%, a rate of formation of N-methyl-α-dimethylaminoacetohydroxamic acid: 86.2%, and a rate of secondary production of N,N-dimethylglycine: 3.3%. Thereafter, by the procedure similar to that in Example 1, 40 g (yield 66.2%) of pure N-methyl-α-dimethylaminoacetohydroxamic acid was obtained. The data of various physical properties were identical with those described in JP-B-6-99382.

Example 3

According to the method described in Example 1, 47.5 g of N-methylhydroxylamine hydrochloride, 23 g of sodium hydroxide, and 66 g of N,N-diethylglycine methyl ester were reacted in a mixture solvent consisting of 55 ml of water and 5.5 ml of 1,2-dimethoxyethane, at 45° C. for 12 hours. The results of gas chromatographic analysis demonstrated a rate of residual raw materials: 12.0%, a rate of formation of N-methyl-α-diethylaminoacetohydroxamic acid: 84.9%, and a rate of secondary production of N,N-diethylglycine: 2.9%. Thereafter, by the procedure similar to that in Example 1, 42.9% (yield 59.0%) of pure N-methyl-α-diethylaminoacetohydroxamic acid was obtained.

Comparative Example 1

To a solution of 88 g of sodium hydroxide dissolved in 440 ml of water, 220 ml of a methanol solution containing 184 g of N-methylhydroxylamine hydrochloride was added, with ice-cooling. After a slightly opaque reaction mixture was stirred, with ice-cooling, for 30 minutes, 257.7 g of N,N-dimethylglycine methyl ester was added thereto. After the resultant reaction mixture was stirred at room temperature for 7 days in total, the raw materials disappeared on a gas chromatographic analysis. A large portion of the solvent was distilled off under a reduced pressure, and thereafter methanol was added to the residue and they were fully shaked, followed by filtration, to remove insoluble substances. The filtrate was concentrated, to obtain a paste-like substance. As a result of gas chromatographic analysis of the resultant substance, it was found that about 36% of N,N-dimethylglycine was mixed therein, and therefore the substance was purified by silica gel column chromatography. Elution was practiced using chloroform/methanol (9/1), and 148 g of solid was obtained. The solid was recrystallized from aceton, to obtain 129.7 g (44.6%) of the first crystal. Further, the solid obtained from a filtrate was also recrystallized from aceton similarly, to obtain 9.4 g of the second crystal. The thus-obtained pure N-methyl-α-dimethylaminoacetohydroxamic acid weighed 139.1 g (yield 47.8%).

Comparative Example 2

To the solution of 131 g of sodium hydroxide dissolved in 400 ml of water, 400 ml of an aqueous solution containing 273 g of N-methylhydroxylamine hydrochloride was added, with ice-cooling. Subsequently, 384 g of N,N-dimethylglycine methyl ester was added thereto. The resultant reaction mixture was stirred at room temperature for 3 days. The results of gas chromatography demonstrated a rate of residual raw materials: 2.3%, a rate of formation of N-methyl-α-dimethylaminoacetohydroxamic acid: 51.5%, and a rate of secondary production of N,N-dimethylglycine: 45.1%. After a large portion of the solvent was distilled off under a reduced pressure, chloroform and then anhydrous magnesium sulfate were added to the residue; thereafter, they were fully shaked, followed by filtration, to remove insoluble substances. After the resultant filtrate was concentrated, the residue was recrystallized from aceton/methanol (50/1), to give 186 g of crystals. As a result of analysis of the crystals using gas chromatography and $^1$H-NMR, it was found that each several percents of each of N,N-dimethylglycine and N-methylhydroxylamine were mixed therein, and therefore the crystals were dissolved again in 3 liters of chloroform, to remove insoluble substances by filtration. After the filtrate was concentrated, the residue was recrystallized from aceton/methanol (12/1), to give 111 g (yield 25.6%) of pure N-methyl-α-dimethylaminoacetohydroxamic acid.

From the Examples and Comparative Examples explained above, it can be understood that the production method of the present invention, in which the reaction is carried out in a mixture system comprising water and an ether-series organic solvent, is short in reaction time, it is good in yield of the objective compound due to less by-product, and it is simplified in production process. Accordingly, both the superiority and the utility (usefulness) of the production method of the present invention are apparent.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method for producing an N-alkyl-α-dialkylaminoacetohydroxamic acid compound represented by formula (2):

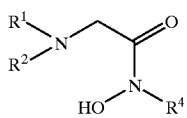

formula (2)

wherein $R^1$ and $R^2$, which are the same or different, each represent an alkyl group, and $R^4$ represents an alkyl group, which comprises reacting an α-dialkylaminoacetic acid ester compound represented by formula (1):

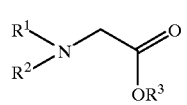

formula (1)

wherein $R^1$ and $R^2$ each have the same meanings as those defined above, and $R^3$ represents an alkyl group, with an N-alkylhydroxylamine, wherein the reaction is carried out in a mixture system comprising water and an ether-series organic solvent.

2. The method as claimed in claim 1, wherein the ether-series organic solvent is at least one solvent selected from the group consisting of diethyl ether, diisopropyl ether, methyl t-butyl ether, diphenyl ether, 1,2-dimethoxyethane, 1,2-diethoxyethane, methoxybenzene, ethoxybenzene, tetrahydrofuran, and 1,4-dioxane.

3. The method as claimed in claim 1, wherein the ether-series organic solvent is at least one solvent selected from the group consisting of 1,2-dimethoxyethane, 1,2-diethoxyethane, methoxybenzene, tetrahydrofuran, and 1,4-dioxane.

4. The method as claimed in claim 1, wherein the reaction temperature is in a range of 20 to 80° C.

5. The method as claimed in claim 1, wherein the compound represented by formula (2) is N-methyl-α-dimethylaminoacetohydroxamic acid or N-methyl-α-diethylaminoacetohydroxamic acid.

6. The method as claimed in claim 1, wherein $R^1$, $R^2$, and $R^3$ in formula (1) and (2) each represent an alkyl group having 1 to 6 carbon atoms.

7. The method as claimed in claim 1, wherein both of $R^1$ and $R^2$ in formula (1) and (2) each are a methyl group at the same time, or an ethyl group at the same time.

8. The method as claimed in claim 1, wherein $R^4$ in formula (2) represents an alkyl group having 1 to 7 carbon atoms.

9. The method as claimed in claim 1, wherein the amount of the solvent is from 0.3 to 100 times that of the α-dialkylaminoacetic acid ester compound in a ratio by weight.

10. The method as claimed in claim 1, wherein a mixing ratio by volume of the organic solvent/water is from ½ to ¹⁄₂₀.

11. The method as claimed in claim 1, wherein the N-alkylhydroxylamine is a free form or a salt thereof.

12. The method as claimed in claim 1, wherein the reaction is carried out in the presence of 0.9 to 1.2 equivalents of an alkali, when an N-alkylhydroxylamine sulfate or an N-alkylhydroxylamine hydrochloride is used as the N-alkylhydroxylamine.

13. The method as claimed in claim 12, wherein the alkali is sodium hydroxide.

14. The method as claimed in claim 1, wherein the number of equivalent, of the N-alkylhydroxylamine to the α-dialkylaminoacetic acid ester compound represented by formula (1) is from 0.9 to 6.0 equivalents.

* * * * *